United States Patent
Oya

(10) Patent No.: US 9,528,960 B2
(45) Date of Patent: Dec. 27, 2016

(54) GAS SENSOR ELEMENT AND GAS SENSOR

(71) Applicant: NGK Spark Plug Co., LTD., Nagoya (JP)

(72) Inventor: Seiji Oya, Niwa (JP)

(73) Assignee: NGK SPARK PLUG CO., LTD., Nagoya (JP)

(*) Notice: Subject to any disclaimer, the term of this patent is extended or adjusted under 35 U.S.C. 154(b) by 395 days.

(21) Appl. No.: 14/271,904

(22) Filed: May 7, 2014

(65) Prior Publication Data

US 2014/0353155 A1    Dec. 4, 2014

(30) Foreign Application Priority Data

May 28, 2013 (JP) .................................. 2013-111549
Mar. 12, 2014 (JP) .................................. 2014-048405

(51) Int. Cl.
*G01N 27/406* (2006.01)
*G01N 27/407* (2006.01)

(52) U.S. Cl.
CPC .................................. *G01N 27/4071* (2013.01)

(58) Field of Classification Search
CPC ....... G01N 27/4071; F01N 2560/00–2560/027
See application file for complete search history.

(56) References Cited

U.S. PATENT DOCUMENTS 6,537,431 B1* 3/2003 Tatsumoto et al. ..... B28B 1/002
                                                            204/421
2006/0151466 A1  7/2006  Diehl
2007/0214865 A1  9/2007  Nakae et al.

FOREIGN PATENT DOCUMENTS

| JP | 61-212754 A   | 9/1986  |
|----|---------------|---------|
| JP | 2002-340845 A | 11/2002 |
| JP | 2003-185622 A | 7/2003  |
| JP | 2007-248219 A | 9/2007  |
| JP | 2009-229449 A | 10/2009 |
| JP | 2010-261727 A | 11/2010 |
| JP | 2012-247390 A | 12/2012 |

OTHER PUBLICATIONS

EPO English language translation of JP 2007-248219 A. Downloaded Sep. 10, 2016.*
Office Action mailed Jul. 21, 2016 for the corresponding Japanese Patent Application No. 2014-048405.

* cited by examiner

*Primary Examiner* — Alexander Noguerola
(74) *Attorney, Agent, or Firm* — Leason Ellis LLP

(57) ABSTRACT

A cross-sectional shape of a gap of a gas sensor element has an end point A which is one of contact points at which the cross-sectional shape is in single-point contact with a virtual straight line parallel to a lamination direction, the one contact point being closest to one side of the laminated structure, an end point B which is one of the contact points closest to another side of the laminated structure, an end point C having the greatest separation from a straight line AB toward a solid electrolyte ceramic layer, and an end point D having the greatest separation from the straight line AB toward another ceramic layer. The distance H1 between the straight line AB and the end point C and the distance H2 between the straight line AB and the end point D satisfy $0.25 \leq H1/H2 < 1.00$ or $1.00 < H1/H2 \leq 4.00$.

12 Claims, 13 Drawing Sheets

| SAMPLE NO. | H1/H2 | H1 : H2 | H1 [μm] | H2 [μm] | H [μm] | THICKNESS OF SOLID ELECTROLYTE CERAMIC LAYER [μm] | INITIAL CRACKING RATIO | THERMAL SHOCK RESISTANCE |
|---|---|---|---|---|---|---|---|---|
| 1-1 | - | 10.0 : 0.0 | 10 | 0 | 10 | 15 | × | - |
| 1-2 | - | 10.0 : 0.0 | 40 | 0 | 40 | 170 | × | - |
| 1-3 | - | 10.0 : 0.0 | 100 | 0 | 100 | 500 | × | - |
| 2-1 | 9.00 | 9.0 : 1.0 | 9 | 1 | 10 | 15 | × | - |
| 2-2 | 9.00 | 9.0 : 1.0 | 36 | 4 | 40 | 170 | × | - |
| 2-3 | 9.00 | 9.0 : 1.0 | 90 | 10 | 100 | 500 | × | - |
| 3-1 | 4.00 | 8.0 : 2.0 | 8 | 2 | 10 | 15 | A | A |
| 3-2 | 4.00 | 8.0 : 2.0 | 32 | 8 | 40 | 170 | A | A |
| 3-3 | 4.00 | 8.0 : 2.0 | 80 | 20 | 100 | 500 | A | B |
| 3-4 | 4.00 | 8.0 : 2.0 | 96 | 24 | 120 | 500 | A | × |
| 4-1 | 1.50 | 6.0 : 4.0 | 6 | 4 | 10 | 15 | A | A |
| 4-2 | 1.50 | 6.0 : 4.0 | 24 | 16 | 40 | 170 | A | A |
| 4-3 | 1.50 | 6.0 : 4.0 | 60 | 40 | 100 | 500 | A | B |
| 4-4 | 1.50 | 6.0 : 4.0 | 72 | 48 | 120 | 500 | A | × |
| 5-1 | 1.22 | 5.5 : 4.5 | 5.5 | 4.5 | 10 | 15 | B | B |
| 5-2 | 1.22 | 5.5 : 4.5 | 22 | 18 | 40 | 170 | B | B |
| 5-3 | 1.22 | 5.5 : 4.5 | 55 | 45 | 100 | 500 | B | B |
| 5-4 | 1.22 | 5.5 : 4.5 | 66 | 54 | 120 | 500 | B | × |
| 6-1 | 1.00 | 5.0 : 5.0 | 5 | 5 | 10 | 15 | × | - |
| 6-2 | 1.00 | 5.0 : 5.0 | 20 | 20 | 40 | 170 | × | - |
| 7-1 | 0.82 | 4.5 : 5.5 | 4.5 | 5.5 | 10 | 15 | B | B |
| 7-2 | 0.82 | 4.5 : 5.5 | 18 | 22 | 40 | 170 | B | B |
| 7-3 | 0.82 | 4.5 : 5.5 | 45 | 55 | 100 | 500 | B | B |
| 7-4 | 0.82 | 4.5 : 5.5 | 54 | 66 | 120 | 500 | B | × |
| 8-1 | 0.67 | 4.0 : 6.0 | 4 | 6 | 10 | 15 | A | A |
| 8-2 | 0.67 | 4.0 : 6.0 | 16 | 24 | 40 | 170 | A | A |
| 8-3 | 0.67 | 4.0 : 6.0 | 40 | 60 | 100 | 500 | A | B |
| 8-4 | 0.67 | 4.0 : 6.0 | 48 | 72 | 120 | 500 | A | × |
| 9-1 | 0.25 | 2.0 : 8.0 | 2 | 8 | 10 | 15 | A | A |
| 9-2 | 0.25 | 2.0 : 8.0 | 8 | 32 | 40 | 170 | A | A |
| 9-3 | 0.25 | 2.0 : 8.0 | 20 | 80 | 100 | 500 | A | B |
| 9-4 | 0.25 | 2.0 : 8.0 | 24 | 96 | 120 | 500 | A | × |
| 10-1 | 0.11 | 1.0 : 9.0 | 1 | 9 | 10 | 15 | × | - |
| 10-2 | 0.11 | 1.0 : 9.0 | 4 | 36 | 40 | 170 | × | - |
| 10-3 | 0.11 | 1.0 : 9.0 | 10 | 90 | 100 | 500 | × | - |
| 11-1 | 0.00 | 0.0 : 10.0 | 0 | 10 | 10 | 15 | × | - |
| 11-2 | 0.00 | 0.0 : 10.0 | 0 | 40 | 40 | 170 | × | - |
| 11-3 | 0.00 | 0.0 : 10.0 | 0 | 100 | 100 | 500 | × | - |

FIG. 7

GAS SENSOR ELEMENT AND GAS SENSOR

This application claims the benefit of Japanese Patent Applications No. 2013-111549 filed May 28, 2013 and No. 2014-048405 filed Mar. 12, 2014, which are incorporated herein by reference in their entity.

FIELD OF THE INVENTION

The present invention relates to a gas sensor element and a gas sensor.

BACKGROUND OF THE INVENTION

A plate-shaped gas sensor element including a plurality of ceramic layers layered together has been known as a gas sensor element used for a gas sensor (see, for example, Japanese Patent Applications Laid-Open (kokai) No. 2010-261727, No. 2003-185622 and No. 2002-340845). Such a gas sensor element includes a solid electrolyte ceramic layer as one of the ceramic layers. Electrodes for detecting a specific gas component contained in an object gas (gas to be to be measured) are formed on the surfaces of the solid electrolyte ceramic layer. A gap for leading a reference gas or the object gas to the corresponding electrode is formed in the gas sensor element. In general, a gas sensor has a heater, and the electric power necessary for heating by the heater can be decreased by reducing the size of the gas sensor.

Problem to be Solved by the Invention

In order to meet the demand for reduction of power consumption, the size of the gas sensor may be reduced by decreasing the height of the gap of the gas sensor element to thereby decrease the thickness of the gas sensor element. However, the gas sensor elements disclosed in Japanese Patent Applications Laid-Open (kokai) No. 2010-261727, No. 2003-185622 and No. 2002-340845 have a problem in that, when the height of the gap of the gas sensor element is decreased, the gas sensor element cracks in a manufacturing stage and fails to have sufficient strength. In particular, in the case of a gas sensor element used in an environment in which a relatively large temperature change occurs (e.g., the exhaust system of an internal combustion engine), even when the gas sensor element does not crack in the manufacturing stage, it may crack due to thermal shock caused by repetition of rapid temperature rising and cooling. Therefore, such a gas sensor element is required to have a sufficient strength against thermal shock (thermal shock resistance).

SUMMARY OF THE INVENTION

Means for Solving the Problems

The present invention has been accomplished so as to solve the above-mentioned problems, and can be realized in the following modes.

(1) According to one mode of the present invention, there is provided a gas sensor element including a plate-shaped laminated structure in which a plurality of ceramic layers, including a solid electrolyte ceramic layer having an electrode formed on a surface thereof, are laminated, the laminated structure having a gap which is formed between the solid electrolyte ceramic layer and a second ceramic layer, extends in a longitudinal direction of the laminated structure, and to which the electrode is exposed. In the gas sensor element, a cross-sectional shape of the gap obtained by cutting the laminated structure along a plane orthogonal to the longitudinal direction has an end point A which is one of contact points at which the cross-sectional shape is in single-point contact with a virtual straight line parallel to a lamination direction of the plurality of ceramic layers, the one contact point being closest to one side surface of the laminated structure extending in the longitudinal direction and the lamination direction, an end point B which is one of the contact points closest to another side surface of the laminated structure opposite the one side surface, an end point C which has the greatest separation from a straight line AB passing through the end point A and the end point B toward the solid electrolyte ceramic layer, and an end point D which has the greatest separation from the straight line AB toward the second ceramic layer. A distance H1 between the straight line AB and the end point C and a distance H2 between the straight line AB and the end point D satisfy a relation $0.25 \leq H1/H2 < 1.00$ or a relation $1.00 < H1/H2 \leq 4.00$, and a height H of the gap which is the sum of the distance H1 and the distance H2 falls within a range of 10 µm to 100 µm. Notably, the cross-sectional shape of the gap is defined by the solid electrolyte ceramic layer and another (second) ceramic layer. According to this mode, it is possible to suppress formation of cracks in the gas sensor element during manufacture thereof. Therefore, it is possible to make the gas sensor element sufficiently strong while decreasing the height of the gap in the gas sensor element. As a result, the thickness of the gas sensor element can be reduced. Also, according to this mode, the height H of the gap falls within the range of 10 µm to 100 µm. Therefore, it is possible to enhance the thermal shock resistance of the gas sensor element while allowing a sufficient amount of air to pass through the gap. When the height H of the gap is less than 10 µm, the gap may fail to allow a sufficient amount of air to pass through the gap. When the height H of the gap is greater than 100 µm, the thermal shock resistance of the gas sensor element deteriorates. Therefore, it is not preferred that the height H of the gap is less than 10 µm or greater than 100 µm.

(2) In the above-described gas sensor element, the distance H1 and the distance H2 may satisfy a relation $0.25 \leq H1/H2 \leq 0.67$ or a relation $1.50 \leq H1/H2 \leq 4.00$. According to this mode, the strength of the gas sensor element can be increased further.

(3) In the above-described gas sensor element, the cross-sectional shape may be convex toward the end point C and also convex toward the end point D. According to this mode, stress generated near the gap can be dispersed. As a result, the strength of the gas sensor element can be increased.

(4) In the above-described gas sensor element, the gap may be an air introduction hole for leading air to the electrode. According to this mode, it is possible to make the gas sensor element sufficiently strong while decreasing the height of the air introduction hole.

(5) In the above-described gas sensor element, the height H may fall within a range of 10 µm to 40 µm. According to this mode, it is possible to further enhance the thermal shock resistance of the gas sensor element while allowing a sufficient amount of air to pass through the gap.

The present invention can be realized in various forms other than the gas sensor element. For example, the present invention can be realized in the form of a gas sensor including the above-described gas sensor element or a manufacturing method of manufacturing the above-described gas sensor element.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIG. 7 is a table showing the results of an evaluation test performed for different values of distances H1 and H2.

DETAILED DESCRIPTION OF THE INVENTION

Mode for Carrying out the Invention

A. Embodiment

A-1. Structure of Gas Sensor

Figure 1:
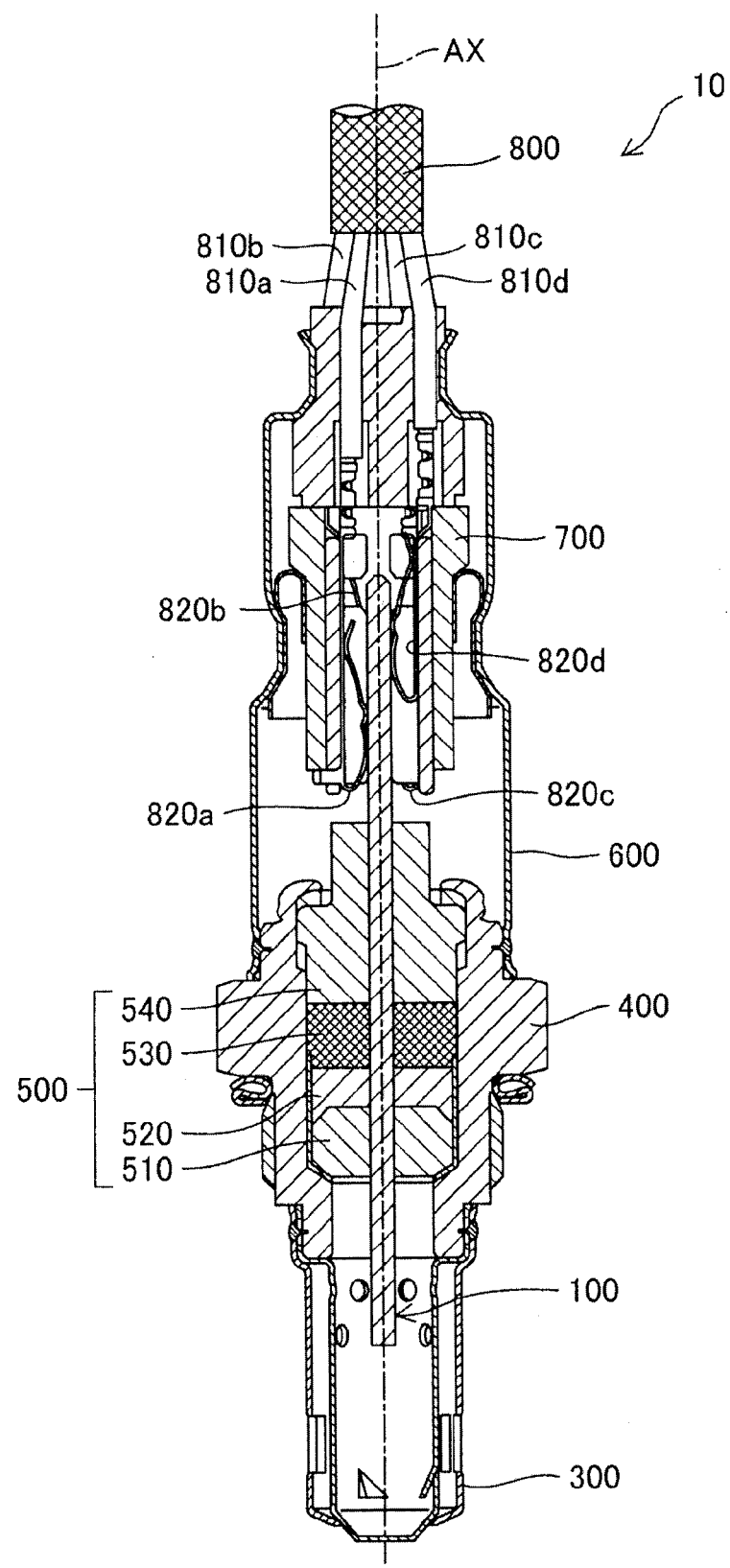
FIG. 1 is a cross-sectional view of a gas sensor.

FIG. 1 is a cross-sectional view of a gas sensor 10. The cross section of FIG. 1 is a cross section obtained by cutting the gas sensor 10 along a plane passing through an axial line AX which is the center axis of the gas sensor 10. In the description of the present embodiment, a side of the gas sensor 10 located on the lower side on the sheet of FIG. 1 will be referred to as a "forward end side," and a side of the gas sensor 10 located on the upper side on the sheet of FIG. 1 will be referred to as a "rear end side."

The gas sensor 10 is an oxygen sensor which is attached to the exhaust system of an internal combustion engine and is adapted to detect oxygen ($O_2$) contained in exhaust gas. The gas sensor 10 includes a gas sensor element 100, a protector 300, a metallic shell 400, an element holding portion 500, an outer tube 600, an insulator 700, and a cable 800.

The gas sensor element 100 of the gas sensor 10 is a plate-shaped laminated ceramic device in which a plurality of ceramic layers are laminated. The gas sensor element 100 constitutes an oxygen concentration cell which outputs electromotive force corresponding to oxygen partial pressure as a sensor output. The details of the gas sensor element 100 will be described later.

The gas sensor element 100 is electrically connected, through the cable 800, to a processing circuit (not shown) for processing the sensor output from the gas sensor element 100. In the present embodiment, the cable 800 includes four lead wires 810a, 810b, 810c, and 810d, and connection terminals 820a, 820b, 820c, and 820d which are electrically connected to the gas sensor element 100 are fixed to the corresponding lead wires by means of crimping. The connection terminal 820a, 820b, 820c, and 820d are mechanically and electrically connected to electrode pads (which will be described later) of the gas sensor element 100, while being pressed against the electrode pads.

The protector 300 of the gas sensor 10 is a metallic member having the shape of a cylindrical tube with a bottom. The protector 300 is fixed to the forward end of the metallic shell 400, and covers the gas sensor element 100 projecting from the forward end of the metallic shell 400. Thus, the protector 300 protects a forward end portion of the gas sensor element 100. The protector 300 has through-holes for introducing an object gas toward the gas sensor element 100.

The metallic shell 400 of the gas sensor 10 is a metallic member having the shape of a cylindrical tube. The gas sensor element 100 is fixedly held inside the metallic shell 400 by the element holding portion 500.

The element holding portion 500 of the gas sensor 10 is a portion for holding the gas sensor element 100 inside the metallic shell 400. The gas sensor element 100 extends through the center of the element holding portion 500. In the present embodiment, the element holding portion 500 includes a ceramic holder 510, a talc ring 520, a talc ring 530, and a ceramic sleeve 540 which are arranged in this order from the forward end side.

The ceramic holder 510 of the element holding portion 500, which is a tubular ceramic member, is inserted into the metallic shell 400, and positions the sensor element 100 inside the metallic shell 400. The talc ring 520 and the talc ring 530 of the element holding portion 500 are formed by compressing talc powder in advance into solid. The talc ring 520 and the talc ring 530 are disposed between the ceramic holder 510 and the ceramic sleeve 540 in a state in which they are pressed forward by the ceramic sleeve 540. The ceramic sleeve 540 of the element holding portion 500 is a tubular ceramic member. The ceramic sleeve 540 is fixed to the rear end of the metallic shell 400 by means of crimping in a state in which the ceramic sleeve 540 is pressed forward, to thereby position the gas sensor element 100 inside the metallic shell 400.

The outer tube 600 of the gas sensor 10 is a metallic member having the shape of a cylindrical tube. The outer tube 600 is welded to the rear end of the metallic shell 400, and covers the gas sensor element 100 projecting from the rear end of the metallic shell 400. Thus, the outer tube 600 protects a rear end portion of the gas sensor element 100. The cable 800 is held at the rear end of the outer tube 600.

The insulator 700 of the gas sensor 10 is a tubular member formed of an electrically insulating ceramic. The insulator 700 is fixedly disposed inside the outer tube 600, and holds the connection terminals 820a, 820b, 820c, and 820d.

A-2. Structure of the Gas Sensor Element

Figure 2:
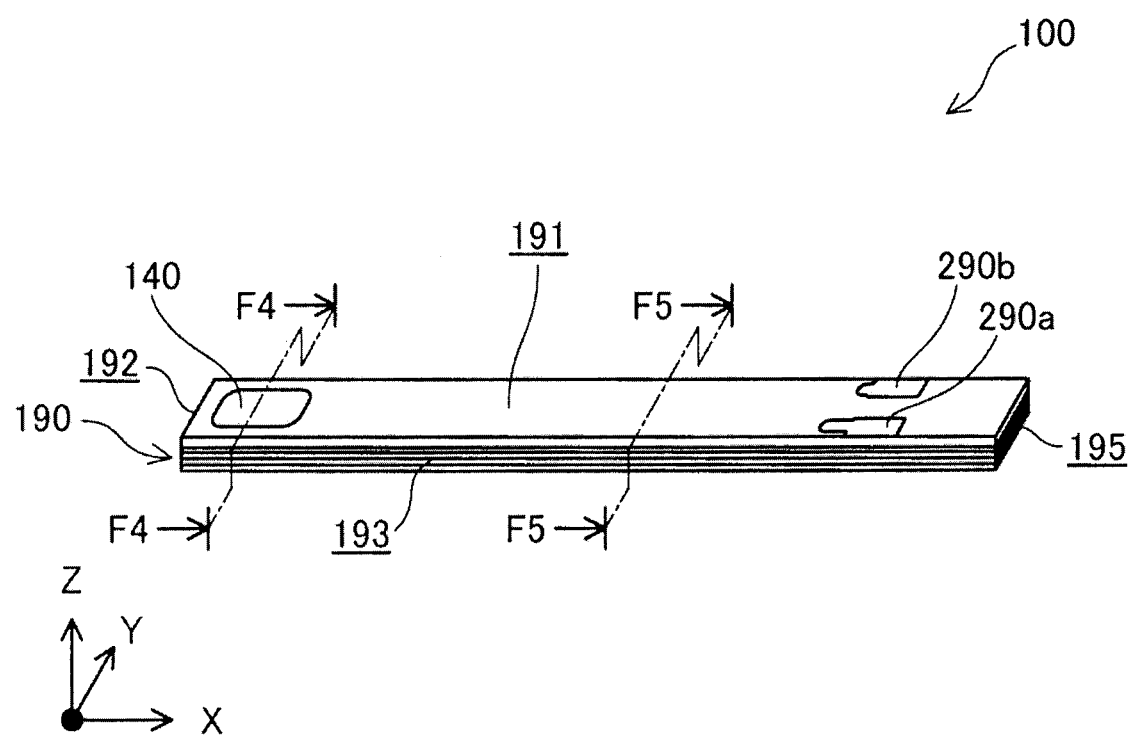
FIG. 2 is an external perspective view of a gas sensor element.
Figure 3:
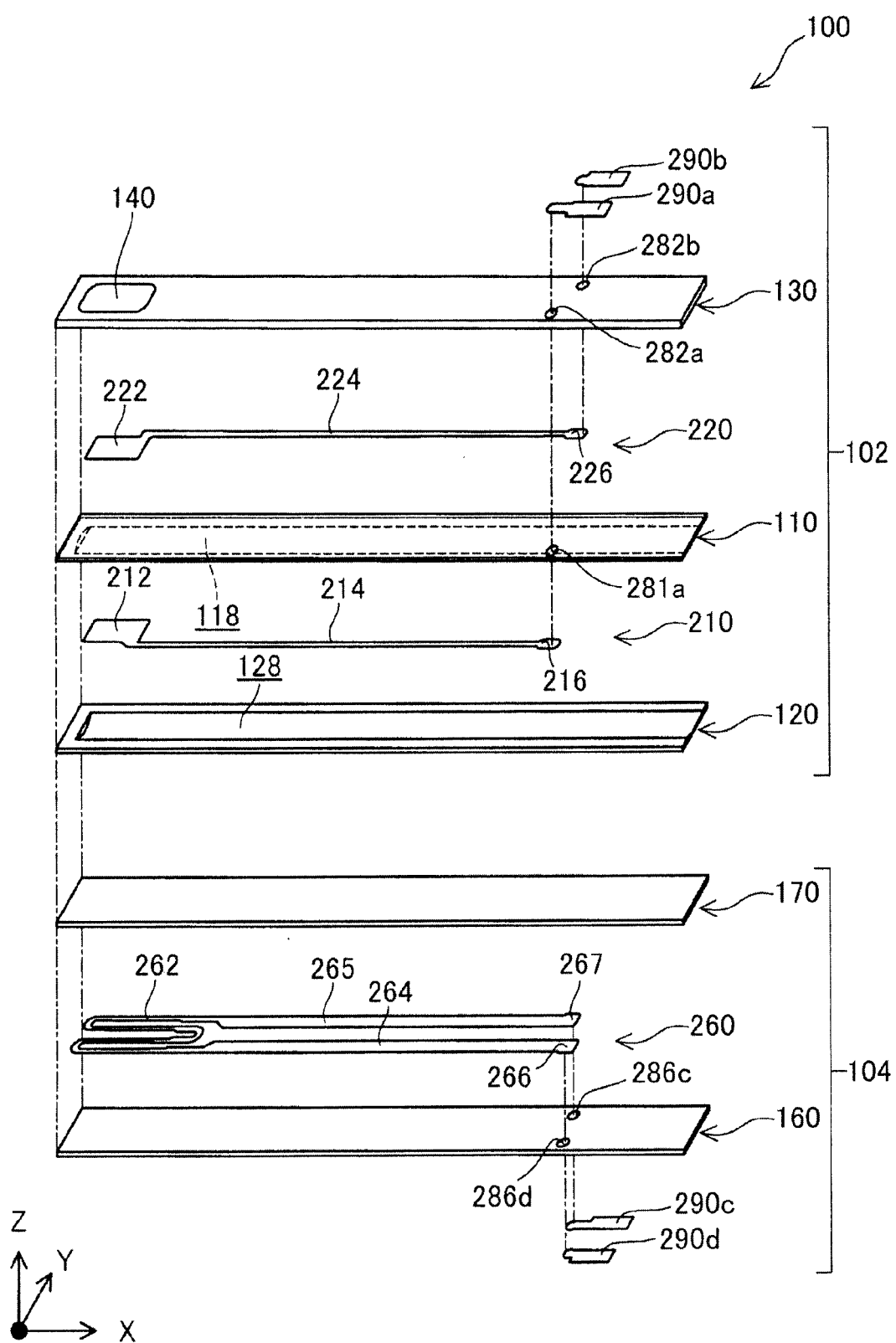
FIG. 3 is an exploded perspective view of the gas sensor element.
Figure 4:
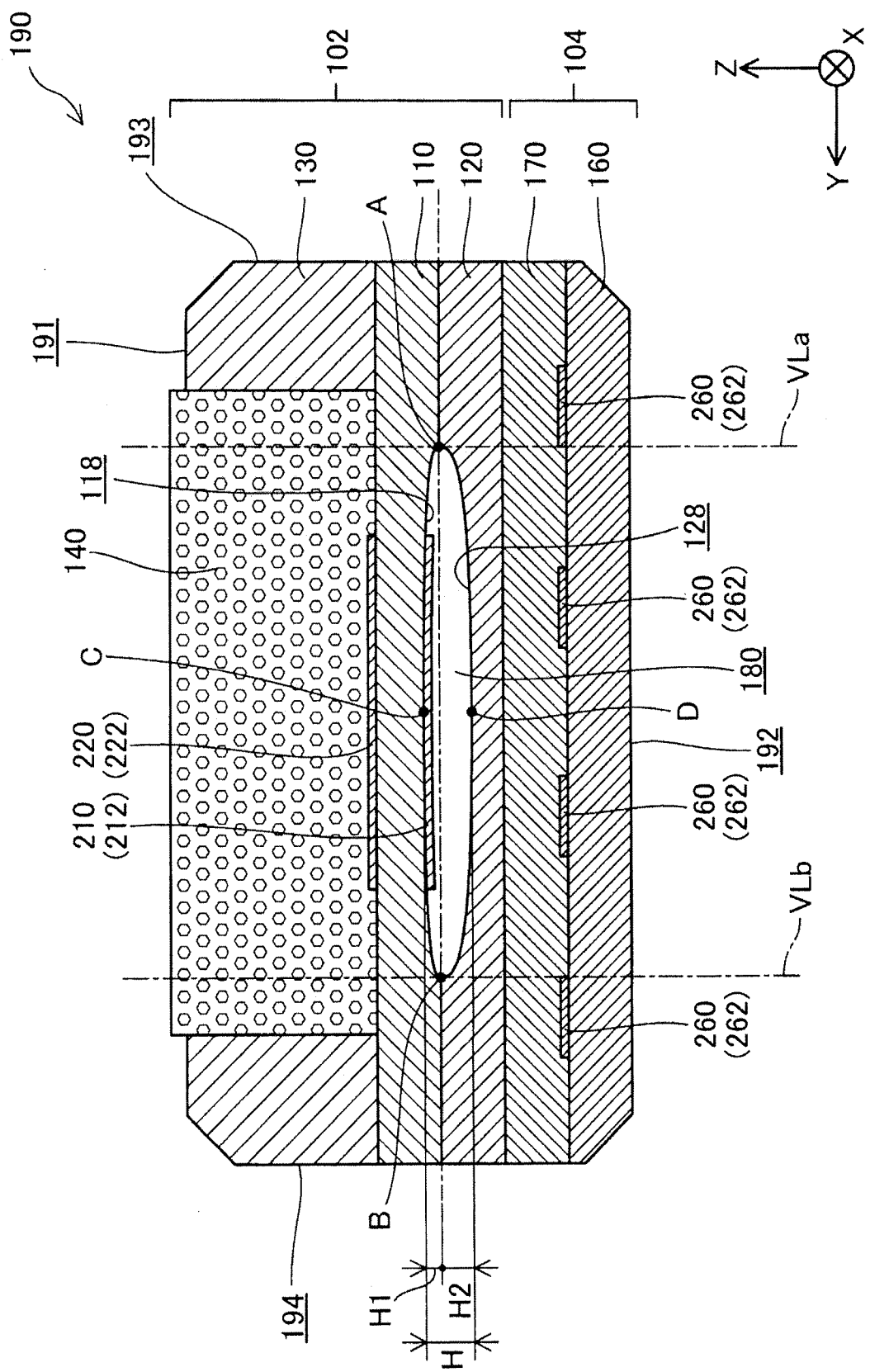
FIG. 4 is a cross-sectional view of the gas sensor element taken along line F4-F4 of FIG. 2.
Figure 5:
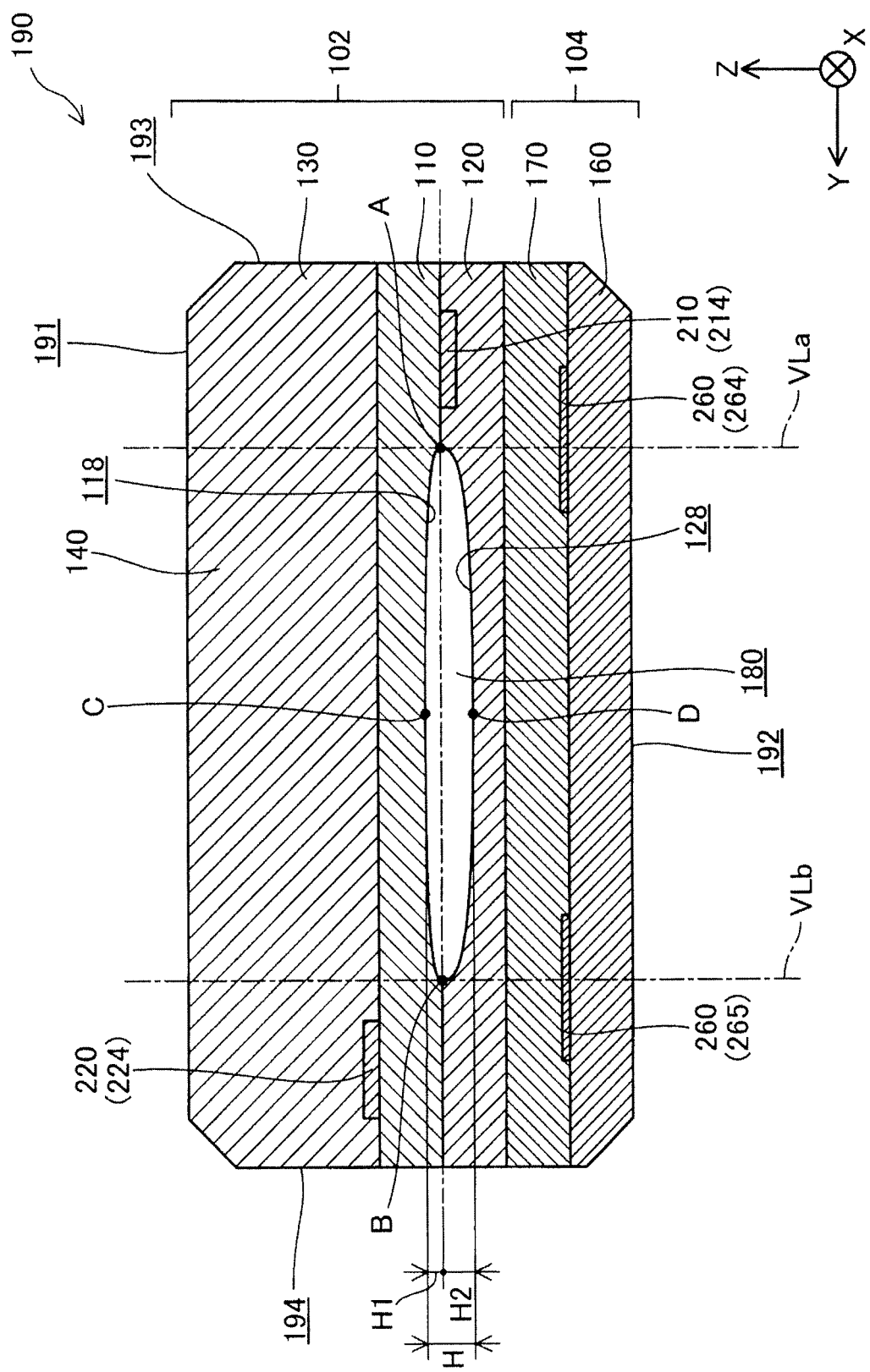
FIG. 5 is a cross-sectional view of the gas sensor element taken along line F5-F5 of FIG. 2.

FIG. 2 is an external perspective view of the gas sensor element 100. FIG. 3 is an exploded perspective view of the gas sensor element 100. FIG. 4 is a cross-sectional view of the gas sensor element 100 taken along line F4-F4 of FIG. 2. FIG. 5 is a cross-sectional view of the gas sensor element 100 taken along line F5-F5 of FIG. 2. X, Y, and Z axes which perpendicularly intersect with one another are shown in FIG. 2. The X, Y, and Z axes of FIG. 2 correspond to the X, Y, and Z axes in other drawings.

Of the X, Y, and Z axes of FIG. 2, the X axis is an axis along the longitudinal direction of the gas sensor element 100. In a state in which the gas sensor element 100 is incorporated into the gas sensor 10, the X axis of the gas sensor element 100 extends along the axial line AX. Of the X-axis directions along the X axis, a +X-axis direction corresponds to an axial direction from the forward end side toward the rear end side (along the axial line AX), and a −X-axis direction is a direction opposite the +X-axis direction.

Of the X, Y, and Z axes of FIG. 2, the Y axis is an axis along the width direction of the gas sensor element 100. Of the Y-axis directions along the Y axis, a +Y-axis direction is a direction from the front side of the sheet of FIG. 2 toward the back side thereof, and a −Y-axis direction is a direction opposite the +Y-axis direction.

Of the X, Y, and Z axes of FIG. 2, the Z axis is an axis along the thickness direction of the gas sensor element 100. Of the Z-axis directions along the Z axis, a +Z-axis direction is a direction from the lower side of the sheet of FIG. 2 toward the upper side thereof, and a −Z-axis direction is a direction opposite the +Z-axis direction.

The gas sensor element 100 has a plate-shaped laminated structure 190 in which a plurality of ceramic layers are laminated together. The laminated structure 190 is a rectangular parallelepiped having outer surfaces 191, 192, 193, 194, 195, and 196.

The outer surface 191 of the laminated structure 190 is a surface facing toward the +Z-axis direction, and the outer surface 192 of the laminated structure 190 is a surface facing toward the −Z-axis direction. The outer surface 193 of the laminated structure 190 is a surface facing toward the −Y-axis direction, and the outer surface 194 of the laminated structure 190 is a surface facing toward the +Y-axis direction. The outer surface 195 of the laminated structure 190 is a surface facing toward the +X-axis direction, and the outer surface 196 of the laminated structure 190 is a surface facing toward the −X-axis direction.

The gas sensor element 100 includes a sensor section 102 for detecting a specific gas component ($O_2$) contained in an object gas (exhaust gas), and a heater section 104 for heating the sensor section 102. In the present embodiment, the heater section 104 is formed as a part of the laminated structure 190 integrally with the sensor section 102. In other embodiments, the heater section 104 may be formed separately from the sensor section 102.

The gas sensor element 100 includes, as the sensor section 102, a solid electrolyte ceramic layer 110, a ceramic layer 120, a ceramic layer 130, a porous portion 140, a conductor layer 210, a conductor layer 220, an electrode pad 290a, and an electrode pad 290b.

A gap 180 extending in the longitudinal direction of the laminated structure 190 (the X-axis direction) is formed between the solid electrolyte ceramic layer 110 and the ceramic layer 120. In the present embodiment, one end of the gap 180 on the +X-axis direction side is opened to the outside at the outer surface 195. Another end of the gap 180 on the −X-axis direction side is closed at a position located inward of the outer surface 194. In the present embodiment, the gap 180 is an air introduction hole for introducing air (reference gas) to the conductor layer 210 which constitutes an electrode.

The solid electrolyte ceramic layer 110 of the gas sensor element 100 is a rectangular plate-shaped ceramic layer. In the present embodiment, the material of the solid electrolyte ceramic layer 110 is yttria partially stabilized zirconia formed by adding yttrium oxide ($Y_2O_3$) into zirconia (zirconium dioxide ($ZrO_2$)). In other embodiments, the material of the solid electrolyte ceramic layer 110 may be partially stabilized zirconia formed by adding into zirconia an oxide(s) of at least one of calcium oxide (CaO), scandium oxide ($Sc_2O_3$), ytterbium oxide ($Yb_2O_3$), gadolinium oxide ($Gd_2O_3$), neodymium oxide ($Nd_2O_3$), and terbium oxide ($Tb_2O_3$).

The conductor layer 210 is formed on the surface of the solid electrolyte ceramic layer 110 located on the −Z-axis direction side. The conductor layer 220 is formed on the surface of the solid electrolyte ceramic layer 110 located on the +Z-axis direction side. A through-hole 281a which is a conductor for electrically connecting the conductor layer 210 and the electrode pad 290a is formed in the solid electrolyte ceramic layer 110. In the present embodiment, the material of the through-hole 281a is platinum (Pt).

A surface 118 which is convex toward the +Z-axis direction side is formed on the −Z-axis direction side of the solid electrolyte ceramic layer 110. The surface 118 defines the +Z-axis direction side of the gap 180.

The ceramic layer 120 of the gas sensor element 100 is a rectangular plate-shaped ceramic layer which has the same size as the solid electrolyte ceramic layer 110, and is laminated on the −Z-axis direction side of the solid electrolyte ceramic layer 110. The ceramic layer 120 is formed of an electrically insulating ceramic. In the present embodiment, the material of the ceramic layer 120 is alumina (aluminum oxide ($Al_2O_3$)).

A surface 128 which is convex toward the −Z-axis direction side is formed on the +Z-axis direction side of the ceramic layer 120. The surface 128 defines the −Z-axis direction side of the gap 180.

The ceramic layer 130 of the gas sensor element 100 is a rectangular plate-shaped ceramic layer which has the same size as the solid electrolyte ceramic layer 110, and is laminated on the +Z-axis direction side of the solid electrolyte ceramic layer 110. The ceramic layer 130 is formed of an electrically insulating ceramic. In the present embodiment, the material of the ceramic layer 130 is alumina.

The electrode pad 290a and the electrode pad 290b are formed on the surface of the ceramic layer 130 located on the +Z-axis direction side. Through-holes 282a and 282b are formed in the ceramic layer 130. The through-hole 282a is a conductor which electrically connects the conductor layer 210 and the electrode pad 290a, and the through-hole 282b is a conductor which electrically connects the conductor layer 220 and the electrode pad 290b. In the present embodiment, conductor paste is charged into the through-holes 282a and 282b, and the material thereof is platinum (Pt).

The porous portion 140 of the gas sensor element 100 is a porous body which has continuous pores and which diffuse the object gas. The porous portion 140 is formed in the ceramic layer 130 at a position near the end thereof located on the −X-axis direction side such that the porous portion 140 extends from the +Z-axis direction side of the ceramic layer 130 to the −Z-axis direction side thereof. The porous portion 140 is formed of an electrically insulating ceramic. In the present embodiment, the material of the porous portion 140 is alumina.

The conductor layer 210 of the gas sensor element 100 is a conductor pattern formed on the −Z-axis direction side of the solid electrolyte ceramic layer 110. In the present embodiment, the material of the conductor layer 210 is platinum (Pt). The conductor layer 210 has an electrode portion 212, a lead portion 214, and a connection portion 216.

The electrode portion 212 of the conductor layer 210 is a rectangular electrode which extends over a region of the surface 118 of the solid electrolyte ceramic layer 110 where the porous portion 140 is present on the +Z-axis direction side. The electrode portion 212 is exposed to the interior of the gap 180. As shown in FIG. 4, in the present embodiment, the surface of the electrode portion 212 on the −Z-axis direction side projects toward the −Z-axis direction side from the surface 118 of the solid electrolyte ceramic layer 110. In other embodiments, the electrode portion 212 may cover the entire region of the surface 118 or may be smoothly connected to the surface 118.

The lead portion 214 of the conductor layer 210 is straight, and connects the electrode portion 212 and the connection portion 216. The connection portion 216 of the conductor layer 210 is wider than the lead portion 214, and is located adjacent to the through-hole 281a of the solid electrolyte ceramic layer 110.

The conductor layer 220 of the gas sensor element 100 is a conductor pattern formed on the +Z-axis direction side of the solid electrolyte ceramic layer 110. In the present embodiment, the material of the conductor layer 220 is platinum (Pt). The conductor layer 220 has an electrode portion 222, a lead portion 224, and a connection portion 226.

The electrode portion 222 of the conductor layer 220 is a rectangular electrode which extends over a region of the +Z-axis direction side boundary surface of the solid electrolyte ceramic layer 110 where the porous portion 140 is present on the +Z-axis direction side. The electrode portion 222 is located adjacent to the porous portion 140. The lead portion 224 of the conductor layer 220 is straight, and connects the electrode portion 222 and the connection portion 226. The connection portion 226 of the conductor layer 220 is wider than the lead portion 224, and is located adjacent to the through-hole 282b of the ceramic layer 130.

The electrode pad 290a of the gas sensor element 100 is a conductor pattern which is formed on the surface of the ceramic layer 130 on the +Z-axis direction side and is located adjacent to the through-hole 282a. In the present embodiment, the material of the electrode pad 290a is platinum (Pt). In a state in which the gas sensor element 100 is incorporated into the gas sensor 10, the electrode pad 290a is mechanically and electrically connected to the connection terminal 820a.

The electrode pad 290b of the gas sensor element 100 is a conductor pattern which is formed on the surface of the ceramic layer 130 on the +Z-axis direction side and is located adjacent to the through-hole 282b. In the present embodiment, the material of the electrode pad 290b is platinum (Pt). In a state in which the gas sensor element 100 is incorporated into the gas sensor 10, the electrode pad 290b is mechanically and electrically connected to the connection terminal 820b.

In the present embodiment, air (reference gas) is supplied to the electrode portion 212 of the conductor layer 210 through the gap 180, and exhaust gas (object gas) is supplied to the electrode portion 222 of the conductor layer 220 through the porous portion 140. The solid electrolyte ceramic layer 110, the electrode portion 212, and the electrode portion 222 constitute an oxygen concentration cell. An electromotive force corresponding to the difference in oxygen partial pressure between the air and the exhaust gas is generated between the electrode portion 212 and the electrode portion 222. The electromotive force generated between the electrode portion 212 and the electrode portion 222 is output to an external circuit or the like through the electrode pad 290a and the electrode pad 290b as a result of detection of oxygen contained in the exhaust gas.

Figure 6:
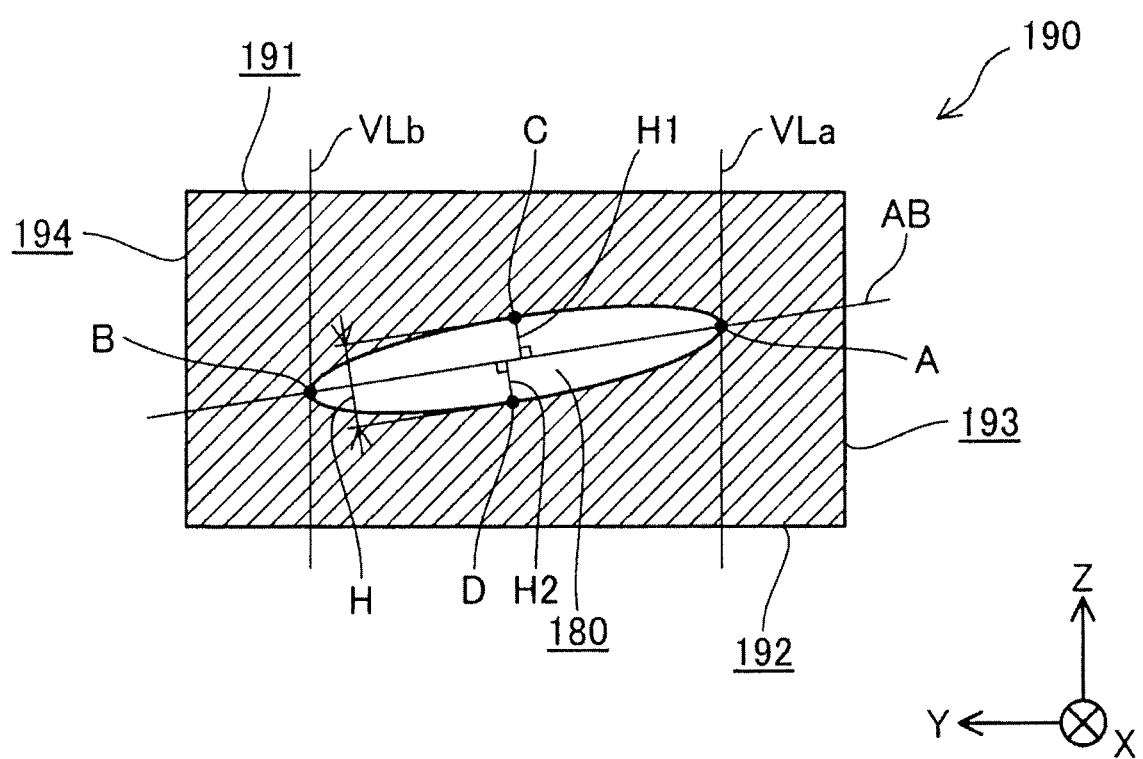
FIG. 6 is an explanatory view schematically showing the cross-sectional shape of a gap.

FIG. 6 is an explanatory view schematically showing the cross-sectional shape of the gap 180. The cross-sectional shape of the gap 180 in FIG. 6 is a cross-sectional shape obtained by cutting the laminated structure 190 along the YZ plane orthogonal to the longitudinal direction (the X-axis direction), and has end points A, B, C, and D. In the present embodiment, the cross-sectional shape of the gap 180 is defined by the solid electrolyte ceramic layer 110 and the ceramic layer 120.

The end point A in the cross-sectional shape of the gap 180 is one of contact points at which the cross-sectional shape of the gap 180 is in single-point contact with a virtual straight line VLa parallel to the lamination direction (the Z-axis direction) of the plurality of ceramic layers in the laminated structure 190, the one contact point being closest to the outer surface 193 of the laminated structure 190. The outer surface 193 of the laminated structure 190 is one of the side surfaces of the laminated structure 190 extending in the longitudinal direction (the X-axis direction) and the lamination direction (the Z-axis direction).

The end point B in the cross-sectional shape of the gap 180 is one of contact points at which the cross-sectional shape of the gap 180 is in single-point contact with a virtual straight line VLb parallel to the lamination direction (the Z-axis direction) of the plurality of ceramic layers in the laminated structure 190, the one contact point being closest to the outer surface 194 of the laminated structure 190. The outer surface 194 of the laminated structure 190 is the other of the side surfaces of the laminated structure 190 extending in the longitudinal direction (the X-axis direction) and the lamination direction (the Z-axis direction).

The end point C in the cross-sectional shape of the gap 180 has the greatest separation from a straight line AB passing through the end point A and the end point B toward the solid electrolyte ceramic layer 110. On the side of the straight line AB toward the +Z-axis direction side, the cross-sectional shape of the gap 180 is convex toward the end point C.

The end point D in the cross-sectional shape of the gap 180 has the greatest separation from the straight line AB passing through the end point A and the end point B toward the ceramic layer 120 (another ceramic layer). On the side of the straight line AB toward the −Z-axis direction side, the cross-sectional shape of the gap 180 is convex toward the end point D.

Preferably, a distance H1 between the straight line AB and the end point C and a distance H2 between the straight line AB and the end point D satisfy a relation $0.25 \leq H1/H2 < 1.00$ or a relation $1.00 < H1/H2 \leq 4.00$. More preferably, the distance H1 and the distance H2 satisfy a relation $0.25 \leq H1/H2 \leq 0.67$ or a relation $1.50 \leq H1/H2 \leq 4.00$. Preferably, the cross-sectional shape of the gap 180 satisfies the above-described relation between the distance H1 and the distance H2 at least in a region where the electrode portion 212 and the electrode portion 222 are present. More preferably, the cross-sectional shape of the gap 180 satisfies the above-described relation in the entire region of the gap 180. The height H of the gap 180 which is the sum of the distance H1 and the distance H2 preferably falls within a range of 10 μm (micrometers) to 100 μm, and more preferably falls within a range of 10 µm to 40 µm. Evaluation on the relation between the distance H1 and the distance H2 will be described later.

In the present embodiment, the distance H1 and the distance H2 satisfy the relation 1.00<H1/H2≤4.00 in the region where the electrode portion 212 and the electrode portion 222 are present as shown in FIG. 4. In the present embodiment, the distance H1 and the distance H2 satisfy the relation 1.00<H1/H2≤4.00 even in a region where the electrode portion 212 and the electrode portion 222 are not present as shown in FIG. 5. Namely, in the present embodiment, over the entire region of the gap 180, the average of radiuses of curvature of the cross-sectional shape of the gap 180 on the +Z-axis direction side of the straight line AB is smaller than the average of radiuses of curvature of the cross-sectional shape of the gap 180 on the −Z-axis direction side of the straight line AB.

The gas sensor element 100 includes, as the heater section 104, a ceramic layer 160, a ceramic layer 170, a conductor layer 260, an electrode pad 290c, and an electrode pad 290d.

The ceramic layer 160 of the gas sensor element 100 is a rectangular plate-shaped ceramic layer which has the same size as the solid electrolyte ceramic layer 110 and which is laminated on the −Z-axis direction side of the ceramic layer 170. The ceramic layer 160 is formed of an electrically insulating ceramic. In the present embodiment, the material of the ceramic layer 160 is alumina.

The conductor layer 260 is formed on the surface of the ceramic layer 160 located on the +Z-axis direction side. The electrode pad 290c and the electrode pad 290d are formed on the surface of the ceramic layer 160 located on the −Z-axis direction side. Through-holes 286c and 286d are formed in the ceramic layer 160. The through-hole 286c is a conductor which electrically connects the conductor layer 260 and the electrode pad 290c, and the through-hole 286d is a conductor which electrically connects the conductor layer 260 and the electrode pad 290d. In the present embodiment, conductor paste is charged into the through-holes 286c and 286d, and the material thereof is platinum (Pt).

The ceramic layer 170 of the gas sensor element 100 is a rectangular plate-shaped ceramic layer which has the same size as the solid electrolyte ceramic layer 110 and which is laminated on the −Z-axis direction side of the ceramic layer 120. The ceramic layer 170 is formed of an electrically insulating ceramic. In the present embodiment, the material of the ceramic layer 170 is alumina.

The conductor layer 260 of the gas sensor element 100 is a conductor pattern formed on the +Z-axis direction side of the ceramic layer 160. In the present embodiment, the material of the conductor layer 260 is platinum (Pt). The conductor layer 260 has a heat generation portion 262, a lead portion 264, a lead portion 265, a connection portion 266, and a connection portion 267.

The heat generation portion 262 of the conductor layer 260 which generates Joule heat is formed in a region of the surface of the ceramic layer 160 located on the +Z-axis direction side where the electrode portion 212 and the electrode portion 222 are present on the +Z-axis direction side. The lead portion 264 of the conductor layer 260 is a straight portion which connects the heat generation portion 262 and the connection portion 266. The lead portion 265 of the conductor layer 260 is a straight portion which connects the heat generation portion 262 and the connection portion 267. The connection portion 266 of the conductor layer 260 is wider than the lead portion 264, and is located adjacent to the through-hole 286d of the ceramic layer 160. The connection portion 267 of the conductor layer 260 is wider than the lead portion 265, and is located adjacent to the through-hole 286c of the ceramic layer 160.

The electrode pad 290c of the gas sensor element 100 is a conductor pattern which is formed on the surface of the ceramic layer 160 on the −Z-axis direction side and is connected to the through-hole 286c. In the present embodiment, the material of the electrode pad 290c is platinum (Pt). In a state in which the gas sensor element 100 is incorporated into the gas sensor 10, the electrode pad 290c is mechanically and electrically connected to the connection terminal 820c.

The electrode pad 290d of the gas sensor element 100 is a conductor pattern which is formed on the surface of the ceramic layer 160 on the −Z-axis direction side and is connected to the through-hole 286d. In the present embodiment, the material of the electrode pad 290d is platinum (Pt). In a state in which the gas sensor element 100 is incorporated into the gas sensor 10, the electrode pad 290d is mechanically and electrically connected to the connection terminal 820d.

A-3. Evaluation Test

FIG. 7 is a table showing the results of an evaluation test performed for different values of the distances H1 and H2. In the evaluation test whose results are shown in FIG. 7, a plurality of gas sensor elements (samples) differing in the ratio between the distance H1 and the distance H2 were manufactured, and the initial cracking ratios and thermal shock resistances of these samples were evaluated. In the evaluation test whose results are shown in FIG. 7, a plurality of samples differing in the distance H1 and the distance H2 were manufactured for each of different ratios between the distance H1 and the distance H2. The ratio between the distance H1 and the distance H2, the distance H1, and the distance H2 of each sample are shown in FIG. 7.

The initial cracking ratio is a ratio of the number of manufactured, unused samples (gas sensor elements) having cracks. The thermal shock resistance is a resistance of each gas sensor element against thermal shock caused by a heat cycle which will be described later.

In a test for evaluating the initial cracking ratio, ten samples which were not used after manufacture thereof were prepared for each of the different ratios between the distance H1 and the distance H2, and a curt surface of each sample was observed through use of a scanning electron microscope (SEM). Criteria for evaluating the initial cracking ratio are as follows.

A (excellent): The initial cracking ratio is 0%.

B (fair): The initial cracking ratio is greater than 0% but not greater than 10%.

x (unacceptable): The initial cracking ratio is greater than 10%.

A test for evaluating the thermal shock resistance was performed on each of the samples which were evaluated as "A (excellent)" or "B (fair)" in the above-described initial cracking ratio evaluation test. In the thermal shock resistance evaluation test, a voltage (21 V) which is 1.5 times the maximum voltage in ordinary use was applied to the heater section of each sample for 10 seconds to thereby heat the sample to about 1000° C. After that, the heated sample was forcedly cooled through use of air for 30 seconds. A cycle (thermal cycle) composed of the heating and the cooling was repeated 1000 times for each sample, and each sample was then checked to determine whether or not it normally functions as a gas sensor element. The thermal cycle composed of the heating and the cooling was further repeated 9000 times for each of the samples normally functioning as a gas sensor element, and each sample was then checked to determine whether or not it normally functions as a gas sensor element. The criteria for evaluating the thermal shock resistance are as follows.

A (excellent): The failure rate after 1000 cycles is 0%, and the failure rate after 10000 cycles is 0%.

B (fair): The failure rate after 1000 cycles is greater than 0% but not greater than 10%.

x (unacceptable): The failure rate after 1000 cycles is greater than 10%.

The results of the evaluation test shown in FIG. 7 reveal that, from viewpoint of the initial cracking ratio, the distance H1 and the distance H2 preferably satisfy the relation 0.25≤H1/H2<1.00 or 1.00<H1/H2≤4.00, and more preferably satisfy the relation 0.25≤H1/H2≤0.67 or 1.50≤H1/H2≤4.00. The results also reveal that, from the viewpoint of the thermal shock resistance, the height H of the gap which is the sum of the distance H1 and the distance H2 preferably falls within the range of 10 μm to 100 μm, and more preferably falls within the range of 10 μm to 40 μm.

Figure 8:
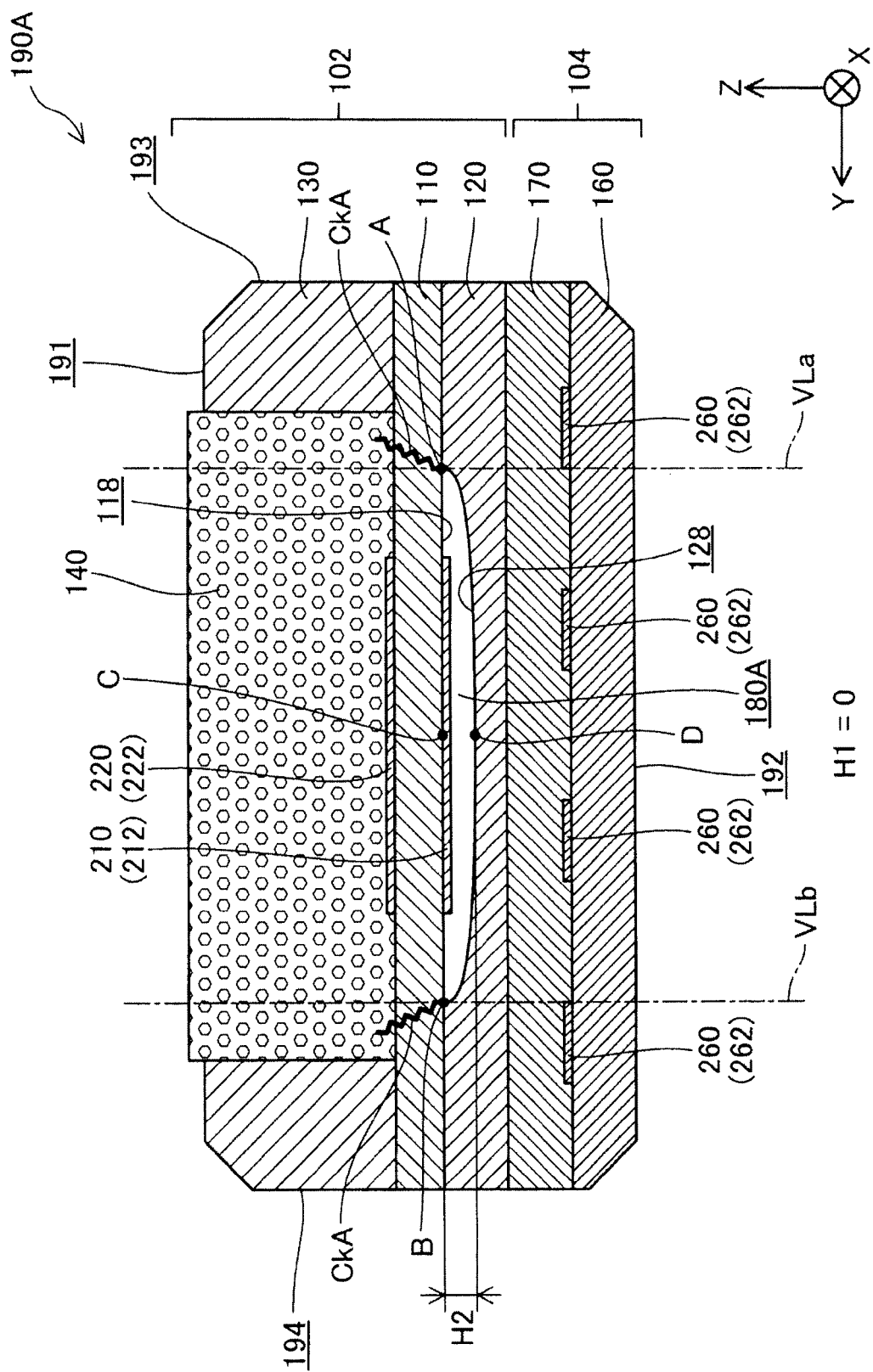
FIG. 8 is a cross-sectional view of a laminated structure of Sample 1.

FIG. 8 is a cross-sectional view of the laminated structure 190A of Sample 11-1. In Sample 11-1, H1=0, and stress around the gap 180A concentrates on the end point A and the end point B. Therefore, cracks CkA are likely to grow from the end point A and the end point B toward the porous portion 140. When the cracks CkA growing from the end point A and the end point B reach the porous portion 140, Sample 11-1 becomes unable to normally function as a gas sensor element.

In contrast to Sample 11-1 in which H1=0, in Sample 1-1, H2=0, and stress concentrates on the end point A and the end point B of the gap of the laminated structure. Therefore, cracks CkA are likely to grow from the end point A and the end point B toward the heater section 104. When the cracks CkA growing from the end point A and the end point B reach the heater section 104, Sample 1-1 becomes unable to normally function as a gas sensor element.

Figure 9:
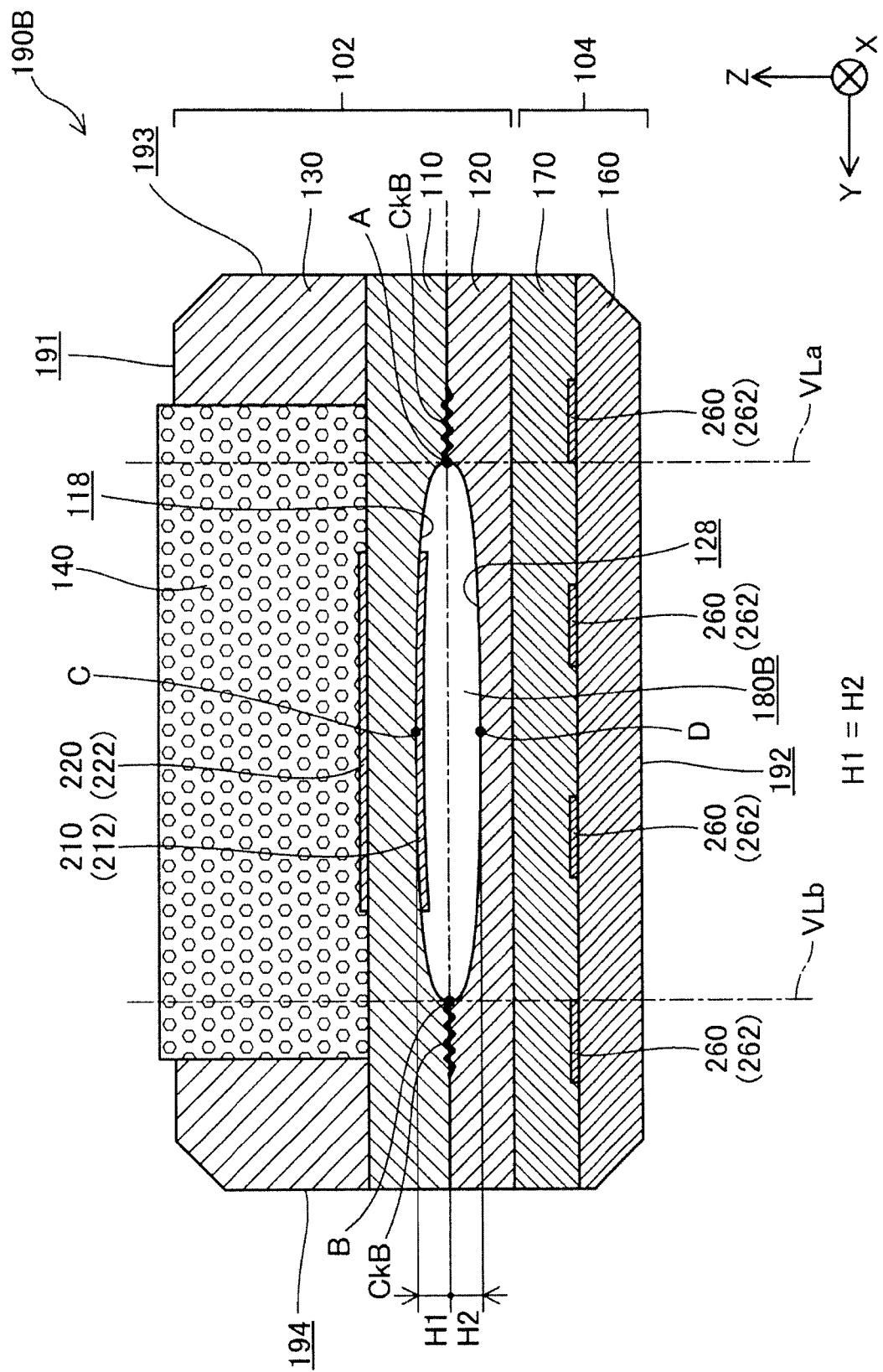
FIG. 9 is a cross-sectional view of a laminated structure of Sample 6.

FIG. 9 is a cross-sectional view of the laminated structure 190B of Sample 6-1. In Sample 6-1, H1=H2, and stress around the gap 180B are dispersed to the surface 118 and the surface 128. However, cracks CkB are likely to grow from the end point A and the end point B toward the outside of the laminated structure 190B (the outer surface 193 and the outer surface 194) along the joint interface between the solid electrolyte ceramic layer 110 and the ceramic layer 120. The strength of the laminated structure 190B is relatively low at the joint interface between the solid electrolyte ceramic layer 110 and the ceramic layer 120. When the cracks CkB growing from the end point A and the end point B reach the outside of the laminated structure 190B, Sample 6-1 becomes unable to normally function as a gas sensor element.

Figure 10:
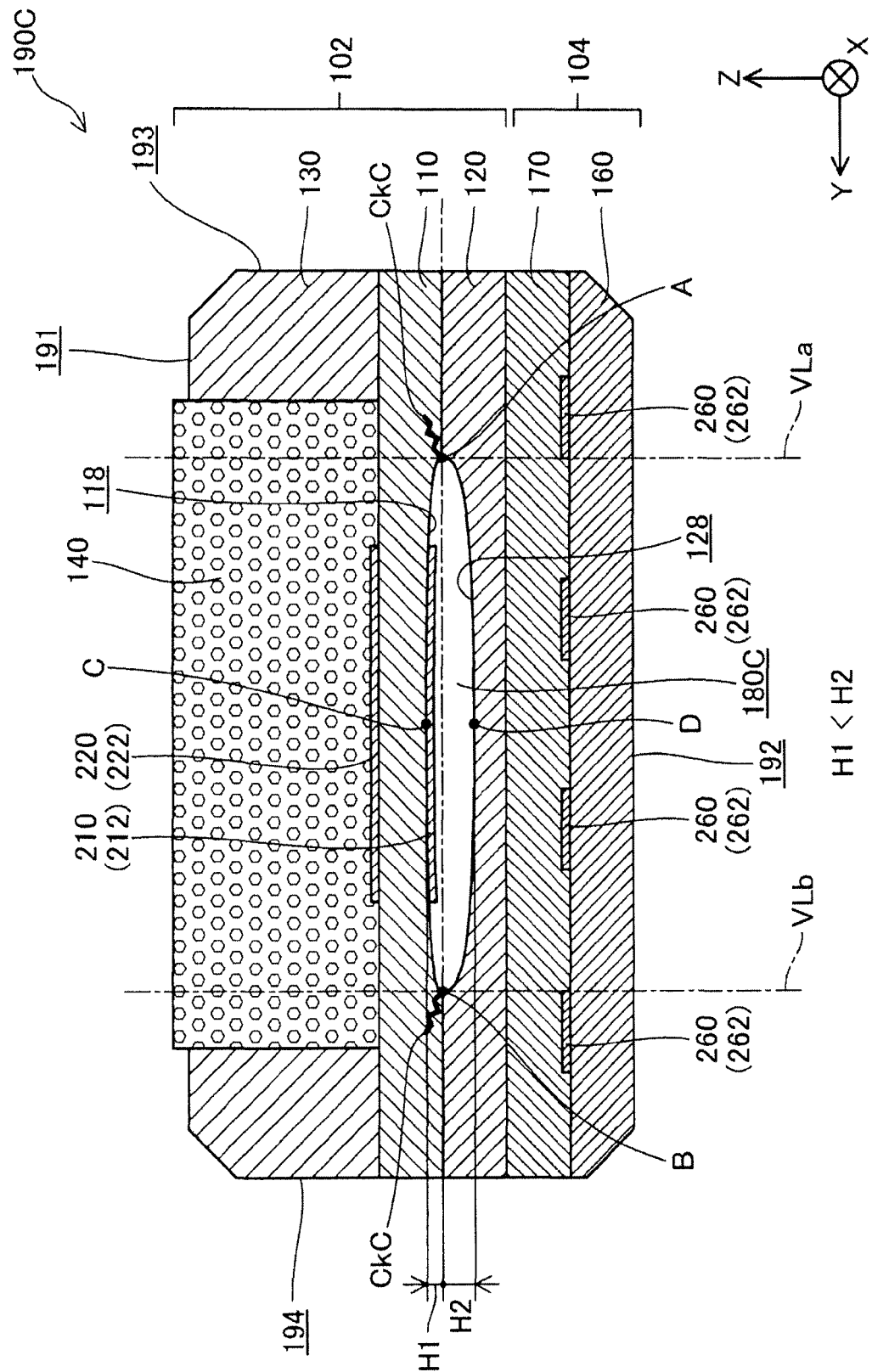
FIG. 10 is a cross-sectional view of a laminated structure of Sample 5.

FIG. 10 is a cross-sectional view of the laminated structure 190C of Sample 7-1. In Sample 7-1, H1<H2, and stress around the gap 180C are dispersed to the surface 118 and the surface 128. Cracks CkC are likely to grow from the end point A and the end point B toward the outside of the laminated structure 190C (the outer surface 193 and the outer surface 194) along directions inclined toward the +Z-axis direction side in relation to the joint interface between the solid electrolyte ceramic layer 110 and the ceramic layer 120. The distances over which the cracks CkC grow from the end point A and the end point B to the outside of the laminated structure 190C in Sample 7-1 are greater than the distances over which the cracks CkB grow from the end point A and the end point B to the outside of the laminated structure 190B in Sample 6-1. Therefore, Sample 7-1 is considered to be superior to Sample 6-1 in terms of initial cracking ratio and thermal shock resistance.

In Samples 8-1 and 9-1, conceivably, generation of cracks is suppressed because stress is dispersed to the surface 118 and the surface 128 to a greater degree as compared with Sample 7-1. Therefore, Samples 8-1 and 9-1 are considered to be superior to Sample 7-1 in terms of initial cracking ratio and thermal shock resistance.

Figure 11:
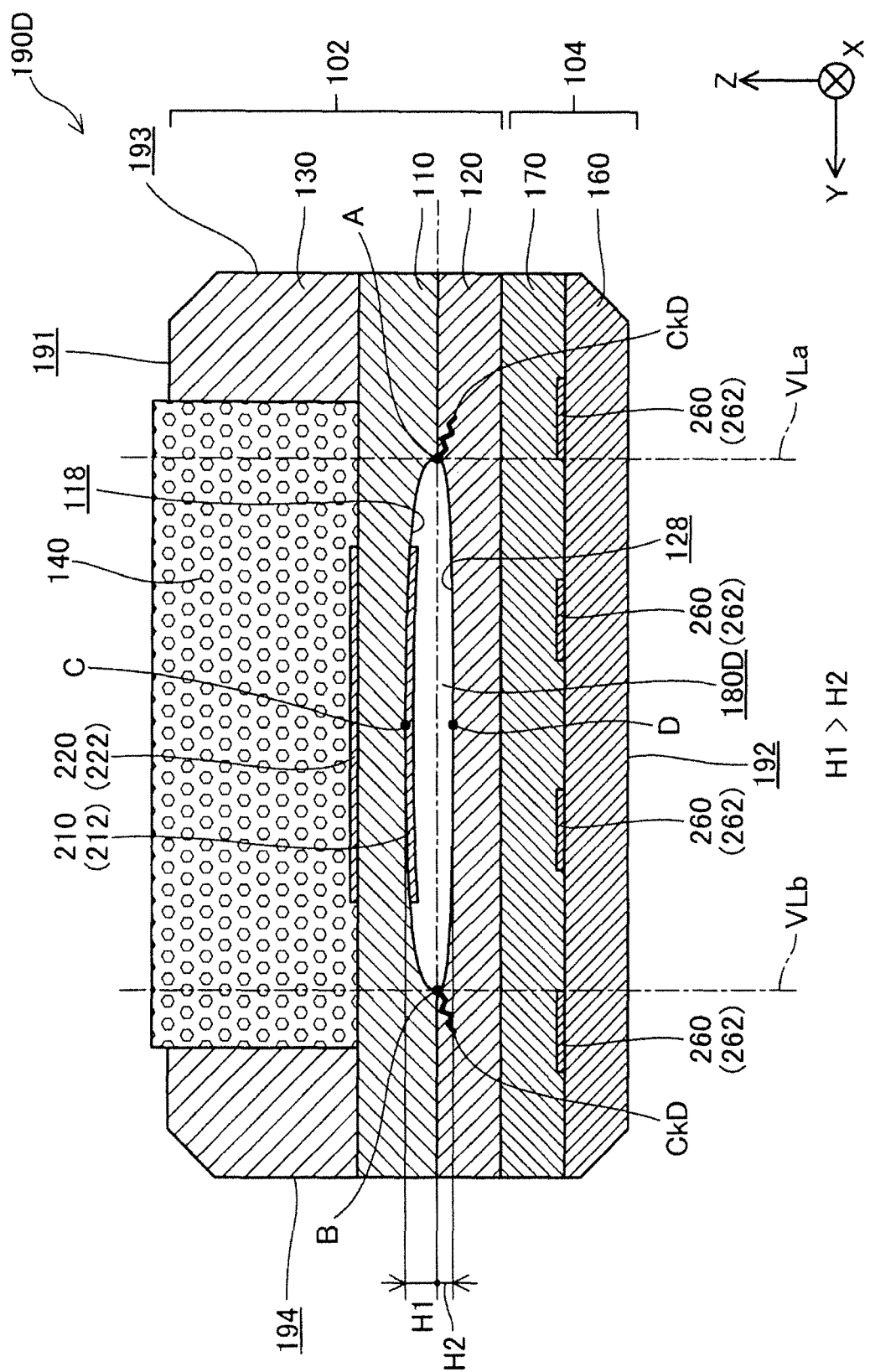
FIG. 11 is a cross-sectional view of a laminated structure of Sample 7.

FIG. 11 is a cross-sectional view of the laminated structure 190D of Sample 5-1. In Sample 5-1, H1>H2, and stress around the gap 180D are dispersed to the surface 118 and the surface 128. Cracks CkD are likely to grow from the end point A and the end point B toward the outside of the laminated structure 190D (the outer surface 193 and the outer surface 194) along directions inclined toward the −Z-axis direction side in relation to the joint interface between the solid electrolyte ceramic layer 110 and the ceramic layer 120. The distances over which the cracks CkD grow from the end point A and the end point B to the outside of the laminated structure 190D in Sample 5-1 are greater than the distances over which the cracks CkB grow from the end point A and the end point B to the outside of the laminated structure 190B in Sample 6-1. Therefore, Sample 5-1 is considered to be superior to Sample 6-1 in terms of initial cracking ratio and thermal shock resistance.

In Samples 3-1 and 4-1, conceivably, generation of cracks is suppressed because stress is dispersed to the surface 118 and the surface 128 to a greater degree as compared with Sample 5-1. Therefore, Samples 3-1 and 4-1 are considered to be superior to Sample 5-1 in terms of initial cracking ratio and thermal shock resistance.

A-4. Method of Manufacturing the Gas Sensor Element

Figure 12:
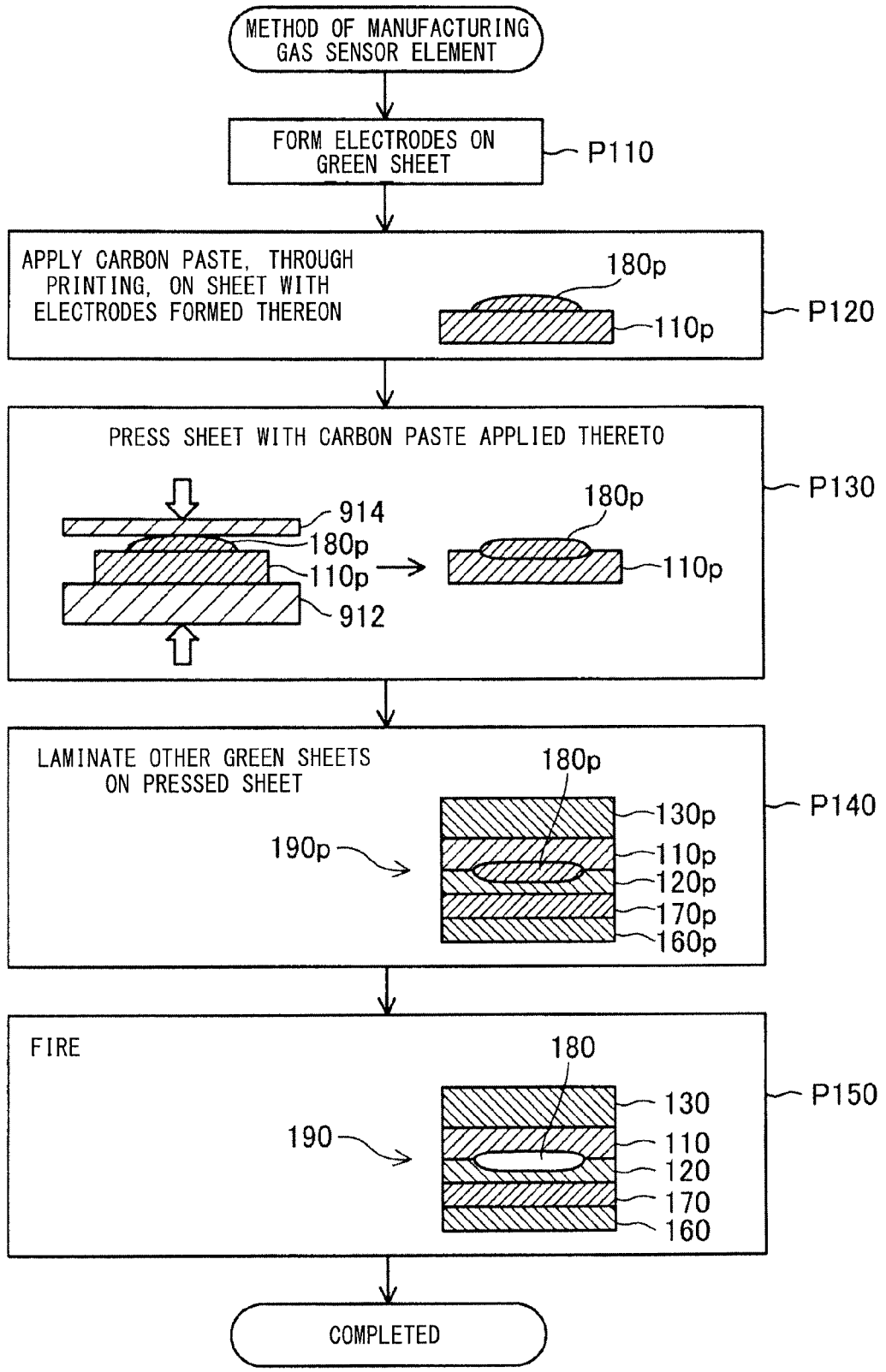
FIG. 12 is a flowchart showing a method of manufacturing a gas sensor element.

FIG. 12 is a flowchart showing a method of manufacturing the gas sensor element 100. When the gas sensor element 100 is manufactured, the conductor layer 210 and the conductor layer 220 are first formed on a green sheet 110p which will become the solid electrolyte ceramic layer 110 (step P110). In the present embodiment, the conductor layer 210 and the conductor layer 220 are formed by applying conductor paste to the green sheet 110p through printing.

After formation of the conductor layer 210 and the conductor layer 220 on the green sheet 110p (step P110), carbon paste 180p is applied, through printing, to a portion of the green sheet 110p where the gap 180 is to be formed (step P120).

After application of the paste 180p to the green sheet 110p through printing (step P120), the green sheet 110p is subjected to press work, whereby the carbon paste 180p is pressed into the green sheet 110p (step P130). In the present embodiment, the press work is performed by pressing the green sheet 110p by plate-shaped dies 912 and 914 which hold the green sheet 110p therebetween.

After the press work (step P130), other green sheets are laminated on the green sheet 110p, whereby a laminated structure 190p is formed (step P140). In the present embodiment, green sheets 120p, 130p, 160p, and 170p which will become the ceramic layers 120, 130, 160, and 170 are laminated on the green sheet 110p.

After formation of the laminated structure 190p (step P140), the laminated structure 190p is fired (step P150). The carbon paste 180p burns and disappears as a result of firing, and the gap 180 is formed at a place where the carbon paste 180p was present. Through these steps, the gas sensor element 100 is completed.

Figure 13:
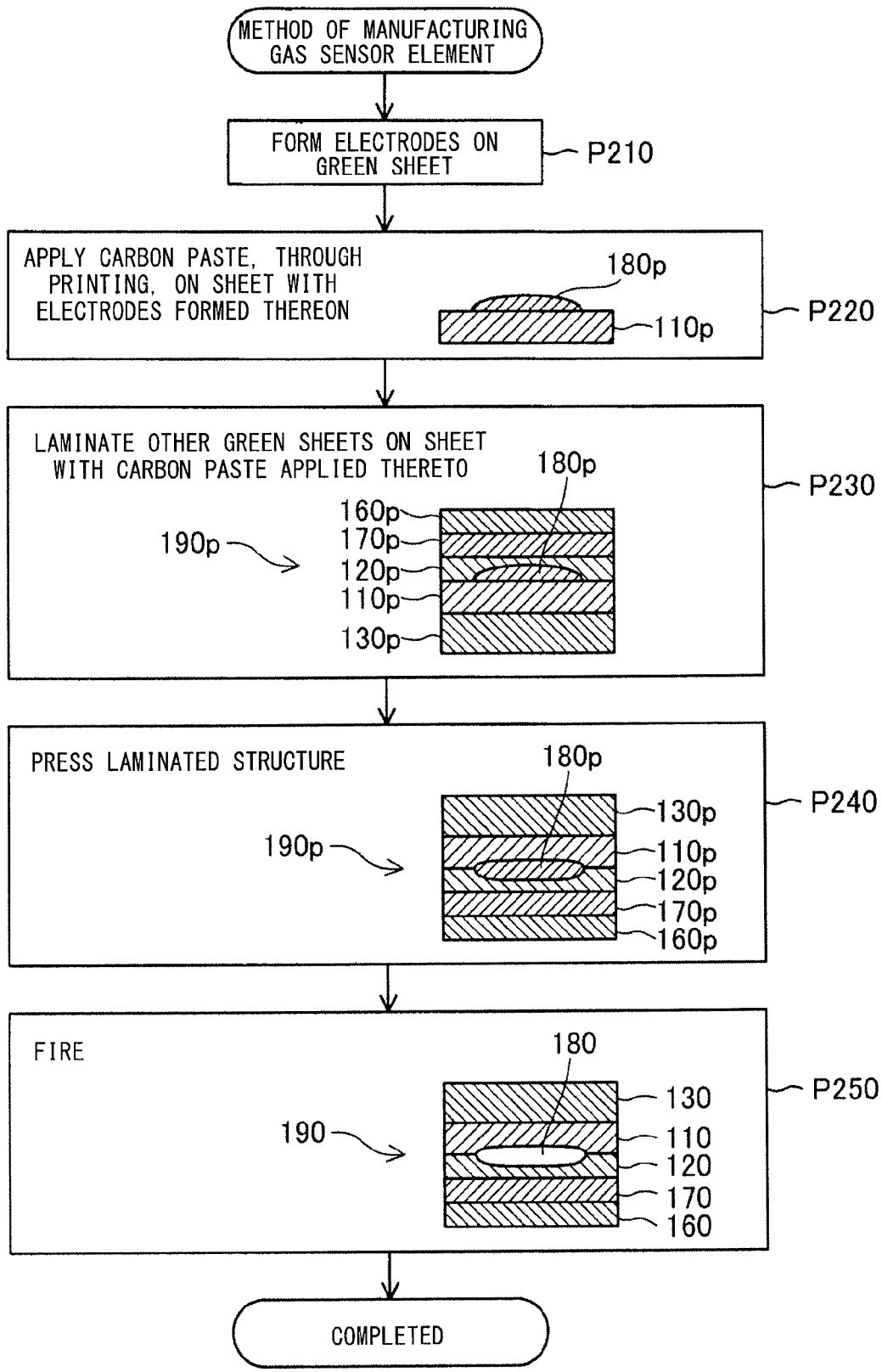
FIG. 13 is a flowchart showing a method of manufacturing a gas sensor element according to another embodiment.

FIG. 13 is a flowchart showing another method of manufacturing the gas sensor element 100. When the gas sensor element 100 is manufactured, the conductor layer 210 and the conductor layer 220 are first formed on a green sheet 110p which will become the solid electrolyte ceramic layer 110 (step P210).

After formation of the conductor layer 210 and the conductor layer 220 on the green sheet 110p (step P210), carbon paste 180p is applied, through printing, to a portion of the green sheet 110p where the gap 180 is to be formed (step P220).

After application of the paste 180p to the green sheet 110p through printing (step P220), other green sheets are laminated on the green sheet 110p, whereby a laminated structure 190p is formed (step P230). Subsequently, the laminated structure 190p is subjected to press work, whereby the carbon paste 180p is pressed into the green sheet 110p (step P240).

After the press work (step P240), the laminated structure 190p is fired (step P250). The carbon paste 180p burns and disappears as a result of firing, and the gap 180 is formed at a place where the carbon paste 180p was present. Through these steps, the gas sensor element 100 is completed.

A-5. Effects

According to the above-described embodiment, the relation $0.25 \leq H1/H2 < 1.00$ or the relation $1.00 < H1/H2 \leq 4.00$ is satisfied. Therefore, it is possible to suppress formation of cracks in the gas sensor element 100 during manufacture thereof. Accordingly, it is possible to make the gas sensor element 100 sufficiently strong while suppressing the height of the gap 180 in the laminated structure 190. As a result, the thickness of the gas sensor element 100 can be reduced. Further, when the relation $0.25 \leq H1/H2 \leq 0.67$ or the relation $1.50 \leq H1/H2 \leq 4.00$ is satisfied, the gas sensor element 100 can have a higher strength. Also, since the cross-sectional shape of the gap 180 is convex toward the end point C and is also convex toward the end point D, stress produced near the gap 180 can be dispersed. As a result, the strength of the gas sensor element 100 can be increased.

Also, when the height H of the gap 180 falls within the range of 10 μm to 100 μm, it is possible to enhance the thermal shock resistance of the gas sensor element 100 while allowing a sufficient amount of air to pass through the gap 180. In particular, when the height H of the gap 180 falls within the range of 10 μm to 40 μm, the thermal shock resistance of the gas sensor element 100 can be enhanced further. Therefore, the height H of the gap 180 falling within such a range is preferred for the gas sensor 10 which is used for the exhaust system of an internal combustion engine which is an environment in which a relatively large temperature change occurs.

B. Other embodiments

The present invention is not limited to the above-described embodiments, examples, and modifications, and can be realized in various configurations without departing from the scope of the invention. For example, the technical features in the embodiments, examples, and modifications which correspond to the technical features of the modes described in the Summary of the Invention section can be freely combined or replaced with other features so as to partially or completely solve the above-described problems or so as to partially or completely yield the above-described effects. Also, a technical feature(s) may be freely omitted unless the technical feature(s) is described in the present specification as an essential feature(s).

The configuration of the gap 180 in the above-described embodiment can be applied not only to an oxygen sensor but also to an NOx sensor which detects nitrogen oxide (NOx). The configuration of the gap 180 in the above-described embodiment can be applied not only to a gap for introducing a reference gas but also to a gap for introducing an object gas.

DESCRIPTION OF REFERENCE NUMERALS

10: gas sensor
100: gas sensor element
102: sensor section
104: heater section
110: solid electrolyte ceramic layer
110p, 120p, 130p, 160p, 170p: green sheet
118, 128: surface
120, 130, 160, 170: ceramic layer
140: porous portion
180, 180A, 180B, 180C, 180D: gap
180p: carbon paste
190, 190A, 190B, 190C, 190D, 190p: laminated structure
191, 192, 193, 194, 195, 196: outer surface
210, 220, 260: conductor layer
212, 222: electrode portion
214, 224, 264, 265: lead portion
216, 226, 266, 267: connection portion
262: heat generation portion
281a, 282a, 282b, 286c, 286d: through-hole
290a, 290b, 290c, 290d: electrode pad
300: protector
400: metallic shell
500: element holding portion
510: ceramic holder
520, 530: talc ring
540: ceramic sleeve
600: outer tube
700: insulator
800: cable
810a, 810b, 810c, 810d: lead wire
820a, 820b, 820c, 820d: connection terminal
912: die
914: die

The invention claimed is:
1. A gas sensor element comprising:
a plate-shaped laminated structure in which a plurality of ceramic layers are laminated, wherein
the plurality of ceramic layers comprise a solid electrolyte ceramic layer having an electrode formed on a surface thereof and a second ceramic layer,
the laminated structure has a gap which is formed between the solid electrolyte ceramic layer and the second ceramic layer, said gap extending in a longitudinal direction of the laminated structure,
the electrode is exposed to the gap,
a cross-sectional shape of the gap obtained by cutting the laminated structure along a plane orthogonal to the longitudinal direction has an end point A which is one of contact points at which the cross-sectional shape is in single-point contact with a virtual straight line parallel to a lamination direction of the plurality of ceramic layers, the one contact point being closest to one side of the laminated structure extending in the longitudinal direction and the lamination direction, an end point B which is one of the contact points closest to another side of the laminated structure opposite the one side, an end point C which has the greatest separation from a straight line AB passing through the end point A and the end point B toward the solid electrolyte ceramic layer, and an end point D which has the greatest separation from the straight line AB toward the second ceramic layer, a distance H1 between the straight line AB and the end point C and a distance H2 between the straight line AB and the end point D satisfy a relation $0.25 \leq H1/H2 < 1.00$ or a relation $1.00 < H1/H2 \leq 4.00$, and a height H of the gap which is the sum of the distance H1 and the distance H2 falls within a range of 10 μm to 100 μm.

2. The gas sensor element according to claim 1, wherein the distance H1 and the distance H2 satisfy a relation $0.25 \leq H1/H2 \leq 0.67$ or a relation $1.50 \leq H1/H2 \leq 4.00$.

3. The gas sensor element according to claim 2, wherein the cross-sectional shape is convex toward the end point C and is also convex toward the end point D.

4. The gas sensor element according to claim 2, wherein the gap is an air introduction hole for leading air to the electrode.

5. The gas sensor element according to claim 2, wherein the height H falls within a range of 10 μm to 40 μm.

6. The gas sensor element according to claim 1, wherein the cross-sectional shape is convex toward the end point C and is also convex toward the end point D.

7. The gas sensor element according to claim 6, wherein the gap is an air introduction hole for leading air to the electrode.

8. The gas sensor element according to claim 3, wherein the height H falls within a range of 10 μm to 40 μm.

9. The gas sensor element according to claim 1, wherein the gap is an air introduction hole for leading air to the electrode.

10. The gas sensor element according to claim 9, wherein the height H falls within a range of 10 μm to 40 μm.

11. The gas sensor element according to claim 1, wherein the height H falls within a range of 10 μm to 40 μm.

12. A gas sensor comprising a gas sensor element according to claim 1.

* * * * *